US007083587B2

(12) United States Patent
Chattopadhyay et al.

(10) Patent No.: US 7,083,587 B2
(45) Date of Patent: Aug. 1, 2006

(54) BLOOD TRANSFUSION SYSTEM

(75) Inventors: Kashi Das Chattopadhyay, Chandigarh (IN); Sanjeev Verma, Chandigarh (IN); Pirthi Raj, Chandigarh (IN); Jitender Gupta, Chandigarh (IN)

(73) Assignee: Counsel of Scientific and Industrial Research, New Delhi (IN)

( * ) Notice: Subject to any disclaimer, the term of this patent is extended or adjusted under 35 U.S.C. 154(b) by 264 days.

(21) Appl. No.: 10/104,166

(22) Filed: Mar. 22, 2002

(65) Prior Publication Data

US 2003/0181841 A1    Sep. 25, 2003

(51) Int. Cl.
*A61M 5/00* (2006.01)
*A61M 37/00* (2006.01)

(52) U.S. Cl. .................. 604/7; 604/6.11; 604/6.12; 604/6.1; 604/6.15

(58) Field of Classification Search ............... 604/6.16, 604/6.15, 6.1, 6.11, 7–10, 6.05, 6.12, 19, 604/131, 151, 236, 38, 35; 422/44; 417/538, 417/258, 489, 545
See application file for complete search history.

(56) References Cited

U.S. PATENT DOCUMENTS

| 1,517,849 | A | * | 12/1924 | McLellan ................ 604/7 |
| 2,689,565 | A | * | 9/1954 | Gobel .................... 604/34 |
| 2,842,124 | A | * | 7/1958 | James .................... 417/437 |
| 4,457,747 | A | * | 7/1984 | Tu ....................... 604/6.12 |
| 4,626,240 | A | * | 12/1986 | Edelman et al. ............. 604/43 |
| 6,106,509 | A | * | 8/2000 | Loubser .................. 604/410 |

* cited by examiner

*Primary Examiner*—Tatyana Zalukaeva
*Assistant Examiner*—Leslie Deak
(74) *Attorney, Agent, or Firm*—Holland & Hart LLP

(57) ABSTRACT

The present invention provides a blood transfusion system having valve circuit, for transfusion of blood to a patient, said system comprising a Y-Shaped connector comprising of three arm [7, 16(*a*) and 16(*b*)] and a junction (9), wherein arm 7 is connected to the patient at its one end and to the junction (9) at its other end, arm 16(*a*) is connected to the junction (9) at its one end and to a waste-blood suction syringe (10) at its other end through a valve (11), an outlet is being provided in the arm 16(*a*) between the valve 11 and the waste-blood suction syringe for dispensing the waste blood, arm 16(*b*) is connected to the junction (9) at its one end and to a fresh-blood supplying syringe (13) at its other end through a valve (14), a fresh-blood supplying means is being connected in the arm 16(*b*) between the valve 14 and the fresh-blood supplying syringe through a valve (15), and syringes (10 and 13) are being operated synchronously.

24 Claims, 2 Drawing Sheets

STROKE 1 : SUCTION STROKE

STROKE 2 : INJECTION STROKE

DEVELOPED BLOOD TRANSFUSION CIRCUIT

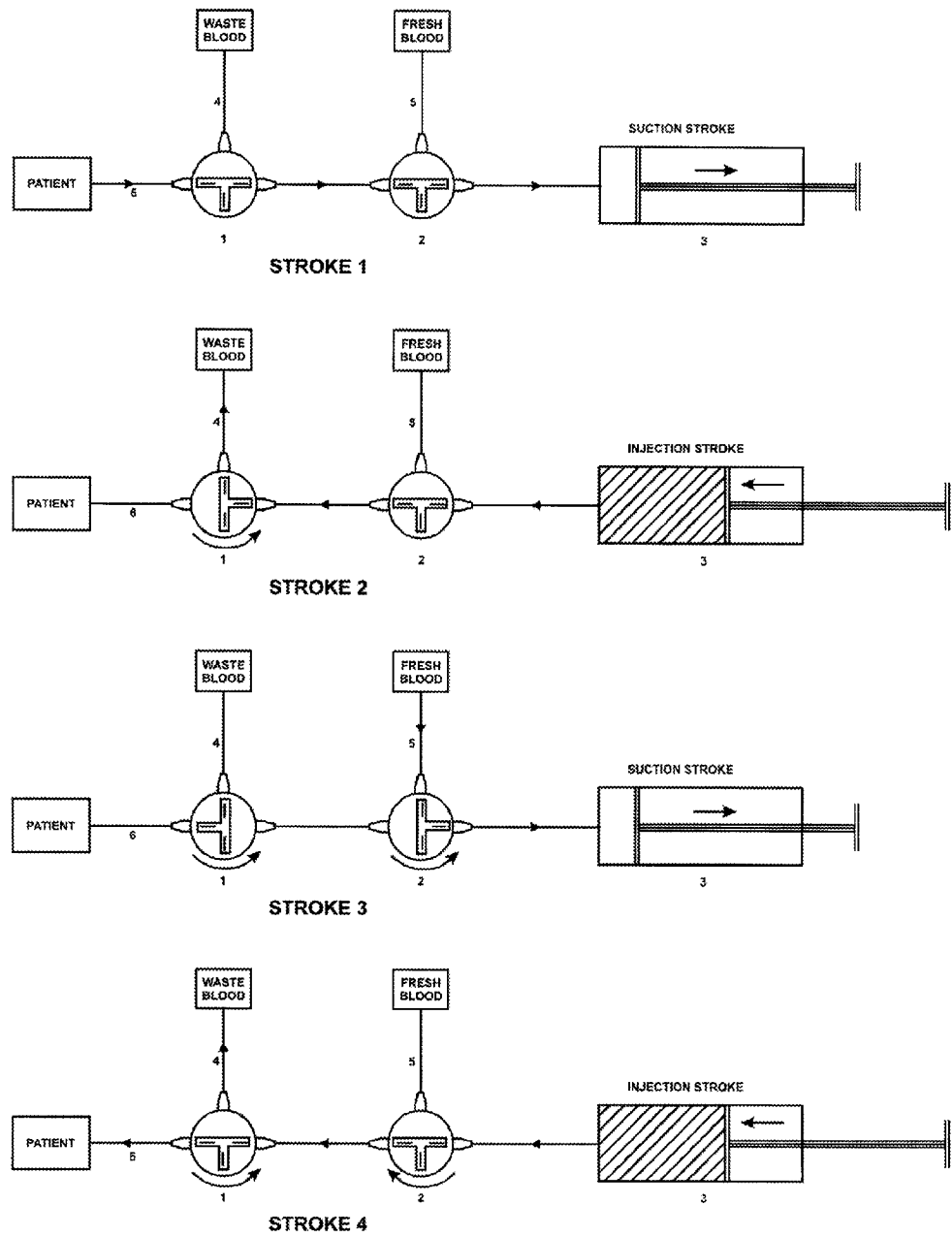
FIGURE 1. PRIOR ART REQUIREMENTS

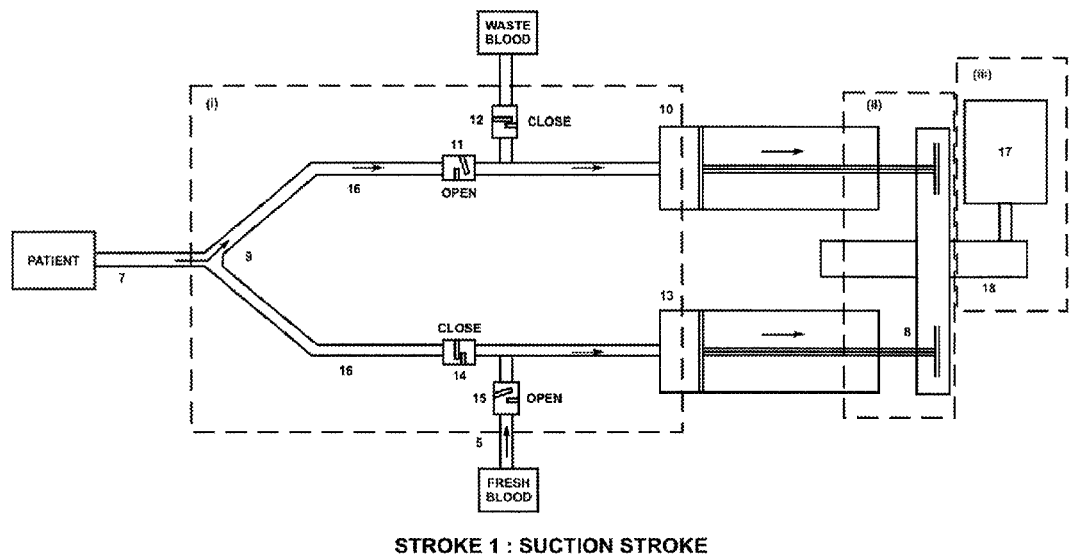
STROKE 1 : SUCTION STROKE
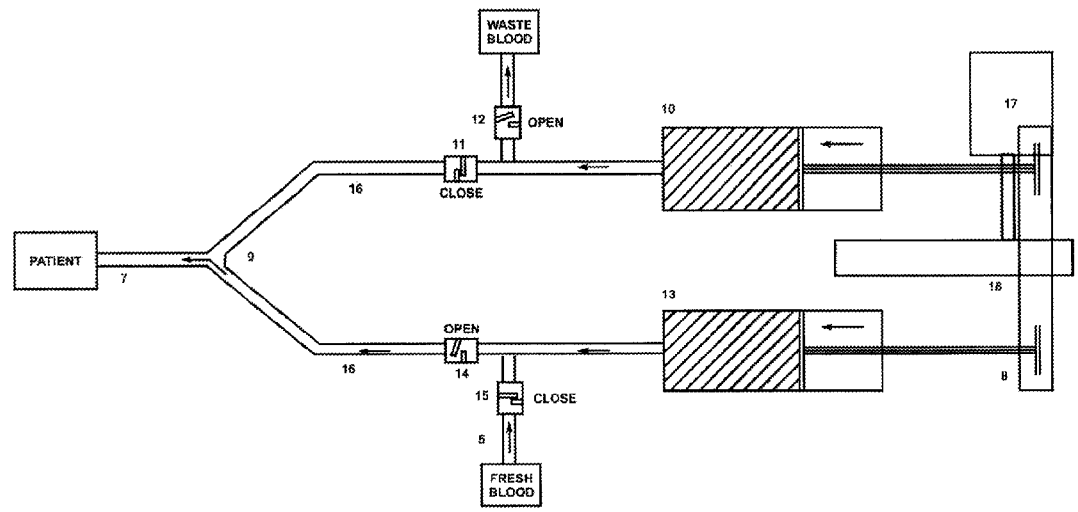
STROKE 2 : INJECTION STROKE
FIGURE 2. DEVELOPED BLOOD TRANSFUSION CIRCUIT

BLOOD TRANSFUSION SYSTEM

FIELD OF THE INVENTION

The present invention provides a blood transfusion system having valve circuit for transfusion of blood to a patient.

BACKGROUND AND PRIOR ART OF THE INVENTION

Blood transfusion is used to exchange the infected blood with fresh blood of Neo-nates who are suffering from jaundice, have some other blood related diseases and for babies whose mothers have 0 (Rh negative) blood group. The blood transfusion requires continuous repetitive cycles of suction of about 5 to 20 ml of infected blood along with simultaneous infusion of same quantity of fresh blood. The blood transfusions are done through the disposable valve and syringes arrangement. The instrument based on this process i.e. Blood Transfusion controller will have several advantages like accuracy and precision in blood transfusion at predetermined rate and initiation of various alarms so as to attract the attention of operator in case of malfunctioning.

BRIEF DESCRIPTION OF THE ACCOMPANYING DRAWING

In the drawings accompanying this specification

FIG. 1 represents the system the various components used in a prior art and its working.

FIG. 2 represents the blood transfusion system of the present invention and its working.

Reference may be made to the present system of blood transfusion in Neonates which requires an expert nurse or doctor to sit continuously for 5–6 hours at the bedside while keeping record of the number of times blood taken out and infused. The prior art requirements are show in FIG. 1 of the drawings attached with this specification. The whole process requires 4 syringe strokes. The circuit uses two 3-way stop-corks (1) and (2) and one syringe (3) and two Intra Venus (I.V.) sets (4) and (5). In the first stroke, infected blood is sucked out by syringe (3) during its outward stroke through a special tube (6) fitted to the umbilical vein of the patient. Stop-cork (1) is rotated manually in such a way that during inward stroke of syringe (3), infected blood goes to the waste bottle through IV set (4). Now, stop-cork (2) is rotated manually in such a way that fresh blood is sucked from the bottle by syringe (3) outward stroke. Then both the stop-cork (1) and (2) are rotated manually such that inward stroke of a syringe (3) infuses the fresh blood to baby through the same tube. As this process requires 5 times rotation of 3-way stop-corks & 4 strokes of syringe for one cycle of infusion and withdrawal, it requires the alertness of the doctor all through the process. Moreover, required proper infusion rate cannot be maintained because of human factor involved, thus promoting the chances of blood cell breakage. It is a very cumbersome process and requires maintaining a proper record of infusion and withdrawal cycles along with quantity. Moreover, as the speed of the suction and infusion of fresh blood varies because of the manual operation, the chances of breakage of blood cells are more. Thus, there is a need to improve the present blood transfusion system.

OBJECTS OF THE PRESENT INVENTION

The main object of the present invention is to provide a blood transfusion system with valve circuit which obviates the drawbacks as detailed above.

Another object of the present invention is to provide an automatic blood transfusion system wherein lesser number of syringe strokes is required.

Still another object of the present invention is to provide an automatic blood transfusion system which will result in minimum involvement of doctor, and that only for checking the functioning of instrument from time to time which obviates the drawback as detailed above.

Yet another object of the present invention is to provide an automatic transfusion system which can infuse blood at required fixed speed thus eliminating chances of breakage of blood cell which obviates the drawback as detailed above.

One more object of the present invention is to provide an automatic transfusion system which can have provision to record, give alarms and display the blood quantity interchanged.

DETAILED DESCRIPTION OF THE PRESENT INVENTION

Accordingly, the present invention provides a blood transfusion system having valve circuit, for transfusion of blood to a patient, said system comprising a Y-shaped connector comprising of three arms [7, 16(a) and 16(b)] and a junction (9), wherein arm 7 is connected to the patient at its one end and to the junction (9) at its other end, arm 16(a) is connected to the junction (9) at its one end and to a waste-blood suction syringe (10) at its other end through a valve (11), an outlet is being provided in the arm 16(a) between the valve 11 and the waste-blood suction syringe for dispensing the waste-blood, arm (16b) is connected to the junction (9) at its one end and to a fresh-blood supplying syringe (13) at its other end through a valve (14), a fresh-blood supplying means is being connected in the arm 16(b) between the valve 14 and the fresh-blood supplying syringe through a valve (15), and syringes (10 and 13) are being operated synchronously.

In an embodiment of the present invention, the arm 7 is connected to umbilical vein of the patient who is a baby.

In another embodiment of the present invention, the valves 11, 14 and 15 are disposable valves.

In yet another embodiment of the present invention, the valves 11, 14 and 15 are one way valves.

In still another embodiment of the present invention, the waste blood sucked out of the patient is collected in a waste-blood collecting means which is linked to the outlet provided on arm 16(a).

In a further embodiment of the present invention, the waste blood collecting means is linked to the outlet through a one-way disposable valve (12).

In one more embodiment of the present invention, the one-way disposable valve 12 is connected to the waste-blood collecting means through intra-venus sets (4).

In one another embodiment of the present invention, the valve 15 is connected to the fresh-blood supplying means through intra-venus set (5).

In any embodiment of the present invention, the operation of the valves 11, 12, 14 and 15 may be controlled manually or using a stepper motor.

In another embodiment of the present invention, waste blood from the patient and fresh blood from the fresh-blood supplying means are sucked simultaneously.

In yet another embodiment of the present invention, fresh blood to the patient and waste-blood to the waste-blood collecting means are pumped simultaneously.

In still another embodiment of the present invention, when waste-blood is sucked from the patient valve 11 is open and valve 12 is closed and when waste blood is pumped to the waste-blood collecting means valve 12 is open and valve 11 is closed.

In a further embodiment of the present invention, wherein when fresh-blood is sucked from fresh-blood supplying means valve 15 is open and valve 14 is closed and when fresh-blood is pumped to the patient valve 14 is open and valve 15 is closed.

In one more embodiment of the present invention, valves 12 and 14 are operated synchronously.

In one another embodiment of the present invention, valves 11 and 15 are operated synchronously.

In an embodiment of the present invention, the syringes may be operated manually or using a syringe driving mechanism.

In another embodiment of the present invention, said syringe driving mechanism comprises of a slider (8) connected to a motor (17) through a means for converting the rotational motion of the motor into linear motion (18).

In yet another embodiment of the present invention, the syringes 10 and 13 may have same capacity or variable capacity.

In still another embodiment of the present invention, the syringes may be replaced to vary the capacity of the blood exchanged in one stroke.

In a further embodiment of the present invention the valve used may be disposable and may be up of Polycarbonate and silicon rubber, which are compatible with medical fluids.

In one more embodiment of the present invention the transfusion may take from umbilical vein through umbilical tube.

In one another embodiment of the present invention the syringe used may be of capacity between 5–20 ml.

In an embodiment of the present invention power supply used for driving the motors may be such as electric mains supply, storage battery, rechargeable battery.

An embodiment of the device of the present invention is shown in FIG. 2 of the drawings accompanying this specification.

The device of the present invention is shown in FIG. 2 of the drawings accompanying this specification. The schematic diagram can be divided into three major parts. They are:

(i) Disposable Valve circuit
(ii) Syringe fixing arrangement
(iii) Syringe driving mechanism 1. Disposable Valve circuit: The circuit constitutes four one-way valves, one umbilical tube, three Y-connectors, two syringes and compatible tubings for various interconnections. The one-way valve are of disposable type and are made for use with medical fluids. These material of construction is Silicon rubber and Polycarbonate. There is no generation of static charge and these can be autoclaved. All tubing consists of standard available L.V. set tubing and makes leak proof joints. It is a low cost system and is easily affordable.

2. Syringe fixing arrangements: Syringes of capacity between 5–25 ml are required to be fixed. Clamping arrangement requires only loosening and tightening of screw after placing syringes in a V-groove.

3. Syringe driving mechanism: It constitutes of motor, slider and driving mechanism. The syringes are clamped with their piston ends in movable slider fixed on a rack. Driving mechanism consists of rack and pinion arrangement.

The operation of the device of present invention is as follows:

Any adult or Pediatric I.V. set available in the market can be used. Tube for connecting with umbilical vein is also available. Insert syringes in the rack with their piston ends in slider (8). Connect all disposable valves, tubings with syringes as per circuit shown in the figure (2) of the drawings accompanying the specifications. Put the fresh blood container at the open end of umbilical tube and at open end of the I.V. set (5). Switch ON the main switch. The motor will start and the syringes will move towards top dead center. One way valves 11 and 15 gets opened and whole system gets filled with fresh blood. During return stroke, valves 12 and 14 get opened. In this way all the air bubbles gets eliminated. Then stop the device when both the syringes are at their bottom dead center. Connect the umbilical vein of the Patient with tube (7). And switch ON the mains. The transfusion cycle starts.

The broad specifications of an embodiment of the device of the present invention may be characterized as follows:

Specifications

Quantity exchanged in one stroke: 5–20 ml
Flow speed: Variable
Mains Power 220V AC, 50 Hz.
System—Fluid conveyance through readily available tubes and syringes and one way valves driven by a stepper motor.

The following examples are given by way of illustration and therefore should not be construed to limit the scope of the present invention.

EXAMPLE 1

Flow rate=20 ml/min. The green liquid was filled exactly 200 ml in the bottle (say patient) and red liquid was filled exactly 200 ml in the bottle (fresh blood). The motor speed was set for 20 ml/min. The liquid was consumed in exactly 10 minutes.

The Main Advantages of the Present Invention are

1. Use of disposable valve circuit.
2. Valves and tubing can be autoclaved and can be used with medical fluids.
3. Cycle with lesser number of syringe strokes.
4. It provides the basis for development of an automatic blood transfusion device which will have minimum involvement of doctor, and that only for checking the functioning of instrument from time to time.
5. It provides the basis for development of an automatic blood transfusion device which can infuse blood at required fixed speed thus eliminating chances of breakage of blood cell.
6. It provides the basis for development of an automatic transfusion device based on the process developed which can record, give alarms and display the blood quantity interchanged.
7. Based on the system developed, an automatic blood transfusion device can be designed and fabricated. It can have several audio and visual alarms to make the system safe and failure proof to the extent possible. Various features which can be incorporated are: LCD display of amount of blood infused and withdrawn and total time elapsed during infusion, selection of flow rate by switches, LCD display for flow rate and alarms, Alarms for Bubble in the flow line, Flow rate high, Operation complete, Leakage in circuit, High Pressure required to infuse. Rechargeable Battery and its indicator should be provided. System should immediately halt if any of the above alarming conditions were observed.

We claim:

1. A blood transfusion system having a valve circuit, for transfusion of blood to a patient, said system comprising a Y-shaped connector comprising three arms [7, 16(a) and 16(b)] and a junction (9), wherein a first arm 7 of the three arms to connect to the patient at one end and connected to the junction (9) at the other end, a second arm 16(a) of the three arms connected to the junction (9) at one end and connected to a waste-blood suction syringe (10) at the other end through a valve (11), an outlet is provided in the second arm 16(a) between the valve 11 and the waste-blood suction syringe for dispensing the waste blood, a third arm (16b) of the three arms connected to the junction (9) at one end and connected to a fresh-blood supplying syringe (13) at the other end through a valve (14), a fresh-blood supplying means connected in to the third arm 16(b) between the valve 14 and the fresh-blood supplying syringe through a valve (15), and waste blood suction syringe (10) and the fresh-blood supplying syringe (13) are operated synchronously.

2. A system as claimed in claim 1, wherein the transfusion uses umbilical cord blood as the fresh-blood supply and the fresh-blood supplying syringe includes an umbilical tube.

3. A blood transfusion system as claimed in claim 1, wherein the valves 11, 14 and 15 are disposable valves.

4. A blood transfusion system as claimed in claim 1, wherein the valves 11, 14 and 15 are one way valves.

5. A blood transfusion system as claimed in claims 1, wherein the valves comprise Polycarbonate and silicon rubber.

6. A blood transfusion system as claimed in claim 1, wherein the waste blood sucked out of the patient is collected in a waste-blood collecting means which is linked to the outlet provided on arm 16(a).

7. A blood transfusion system as claimed in claim 6, wherein the waste blood collecting means is linked to the outlet through a one-way disposable valve (12).

8. A blood transfusion system as claimed in claim 7, wherein the one-way disposable valve 12 is connected to the waste-blood collecting means through intra-venus sets (4).

9. A blood transfusion system as claimed in claim 1, wherein the valve 15 is connected to the fresh-blood supplying means through intra-venus set (5).

10. A blood transfusion system as claimed in claim 1, wherein the operation of the valves 11, 12, 14 and 15 is controlled manually.

11. A blood transfusion system as claimed in claim 1, wherein waste blood from the patient and fresh blood from the fresh-blood supplying means are sucked simultaneously.

12. A blood transfusion system as claimed in claim 1, wherein fresh blood to the patient and waste-blood to the waste-blood collecting means are pumped simultaneously.

13. A blood transfusion system as claimed in claim 1, wherein when waste-blood is sucked from the patient valve 11 is opened and valve 12 is closed and when waste blood is pumped to the waste-blood collecting means valve 12 is open and vale 11 is closed.

14. A blood transfusion system as claimed in claim 1, wherein when fresh-blood is sucked from fresh-blood supplying means valve 15 is open and valve 14 is closed and when fresh-blood is pumped to the patient valve 14 is open and valve 15 is closed.

15. A blood transfusion system as claimed in claim 1, wherein valves 12 and 14 are operated synchronously.

16. A blood transfusion system as claimed in claim 1, wherein valves 11 and 15 are operated synchronously.

17. A blood transfusion system as claimed in claim 1, wherein the syringes are operated manually.

18. A blood transfusion system as claimed in claim 17, wherein said syringe driving mechanism comprises of a slider (8) connected to a motor (17), driven by a power supply, through a means for converting the rotational motion of the motor into linear motion (18).

19. A system as claimed in claim 18, wherein the power supply used for driving the motors is selected from a group of power supplies consisting of electric mains supply, storage battery, or rechargeable battery.

20. A blood transfusion system as claimed in claim 1, wherein the syringes 10 and 13 have variable capacity.

21. A system as claimed in claim 20, wherein the syringes have capacity between 5–20 ml.

22. A system as claimed in claim 1, wherein replacing the syringes varies the capacity of the blood exchanged in one stroke.

23. A blood transfusion system as claimed in claim 1, wherein the operation of the valves 11, 12, 14 and 15 is controlled using a stepper motor.

24. A blood transfusion system as claimed in claim 1, wherein the syringes are operated using a driving mechanism.

* * * * *

UNITED STATES PATENT AND TRADEMARK OFFICE
CERTIFICATE OF CORRECTION

PATENT NO. : 7,083,587 B2 Page 1 of 1
APPLICATION NO. : 10/104166
DATED : August 1, 2006
INVENTOR(S) : Kashi Das Chattopadhyay It is certified that error appears in the above-identified patent and that said Letters Patent is hereby corrected as shown below:

Title page 1, In code (73) Assignee, delete "Counsel" and insert --Counsil--

Signed and Sealed this

Twenty-sixth Day of June, 2007

JON W. DUDAS
*Director of the United States Patent and Trademark Office*